(12) United States Patent
Tucker

(10) Patent No.: US 8,916,605 B2
(45) Date of Patent: Dec. 23, 2014

(54) COMPOUNDS AND METHODS FOR TREATING CANCER AND VIRAL INFECTIONS

(76) Inventor: William G. Tucker, Charlottetown (CA)

( * ) Notice: Subject to any disclaimer, the term of this patent is extended or adjusted under 35 U.S.C. 154(b) by 348 days.

(21) Appl. No.: 13/254,014

(22) PCT Filed: Mar. 2, 2010

(86) PCT No.: PCT/CA2010/000281
§ 371 (c)(1),
(2), (4) Date: Sep. 28, 2011

(87) PCT Pub. No.: WO2010/099600
PCT Pub. Date: Sep. 10, 2010

(65) Prior Publication Data
US 2012/0035238 A1 Feb. 9, 2012

Related U.S. Application Data

(60) Provisional application No. 61/156,560, filed on Mar. 2, 2009.

(51) Int. Cl.
| | | |
|---|---|---|
| *A01N 43/38* | (2006.01) | |
| *A01N 43/36* | (2006.01) | |
| *A61K 31/40* | (2006.01) | |
| *C07D 401/00* | (2006.01) | |
| *A61K 31/4035* | (2006.01) | |

(52) U.S. Cl.
CPC .............. *A61K 31/40* (2013.01); *A61K 31/4035* (2013.01)
USPC .......................... 514/417; 514/423; 546/277.1

(58) Field of Classification Search
USPC ................... 514/417, 423; 546/277.1
See application file for complete search history.

(56) References Cited

FOREIGN PATENT DOCUMENTS

| WO | 2004106493 A2 | 12/2004 |
|---|---|---|
| WO | 2009/019561 A2 | 2/2009 |

OTHER PUBLICATIONS

Moon et al. Biochimica et biophysica Acta (BBA)-Protein Structure & Molecular Enzymology, 1987, vol. 914, Issue 1, Abstract.*
Golub et al., Science, vol. 286, Oct. 15, 1999, pp. 531-537.*
Lin, Huey-Shin, Weinkam, Robert J., "Metabolisn of 1,3-Bis(2-chloroethyl)-1-nitrosourea by Rat Hepatic Microsomes", J. Med. Chem., 1981, 24, 761.
Bruggemann, Svenja K.; Kisro, Jens; Wagner, Thomas, "Ifosfamide Cytotoxicity on Human Tumor and Renal Cells: Role of Chloroacetaldehyde in Comparison to 4-Hydroxyifosfamide", Cancer Research, 57, 2676-2680, Jul. 1, 1997.
STN Search Transcript, Jun. 5, 2007.
STN Search Transcript, Feb. 10, 2009.
STN Search Transcript, May 29, 2007.
Shoji, S., et al., "N-Fatty Acyl Compounds Inhibit Myristoyl Acylation of PP60V-SRC and Reduce Tumorigenicity of Rous Sarcoma Virus-Infected Cells", Biochemistry International, vol. 23, No. 1, Jan. 1, 1991, pp. 15-23.
Burkman A.M., et al. "Some Pharmacological and Toxicological Properties of Several Phthalimidoaldehydes", Journal of Pharmaceutical Sciences, vol. 57, No. 5, May 1, 1968, pp. 815-819.
Extended European Search Report of EP 10748252.3, Jan. 10, 2012.

* cited by examiner

*Primary Examiner* — Samira Jean-Louis
(74) *Attorney, Agent, or Firm* — Bereskin & Parr LLP/S.E.N.C.R.L., s.r.l.; Patricia Folkins

(57) ABSTRACT

The present application relates to the use of one or more compounds of Formula (I) or pharmaceutically acceptable solvates or prodrugs thereof, for treating cancer or for treating or preventing a viral infection.

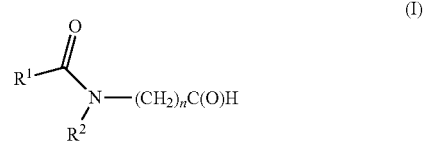

7 Claims, 1 Drawing Sheet

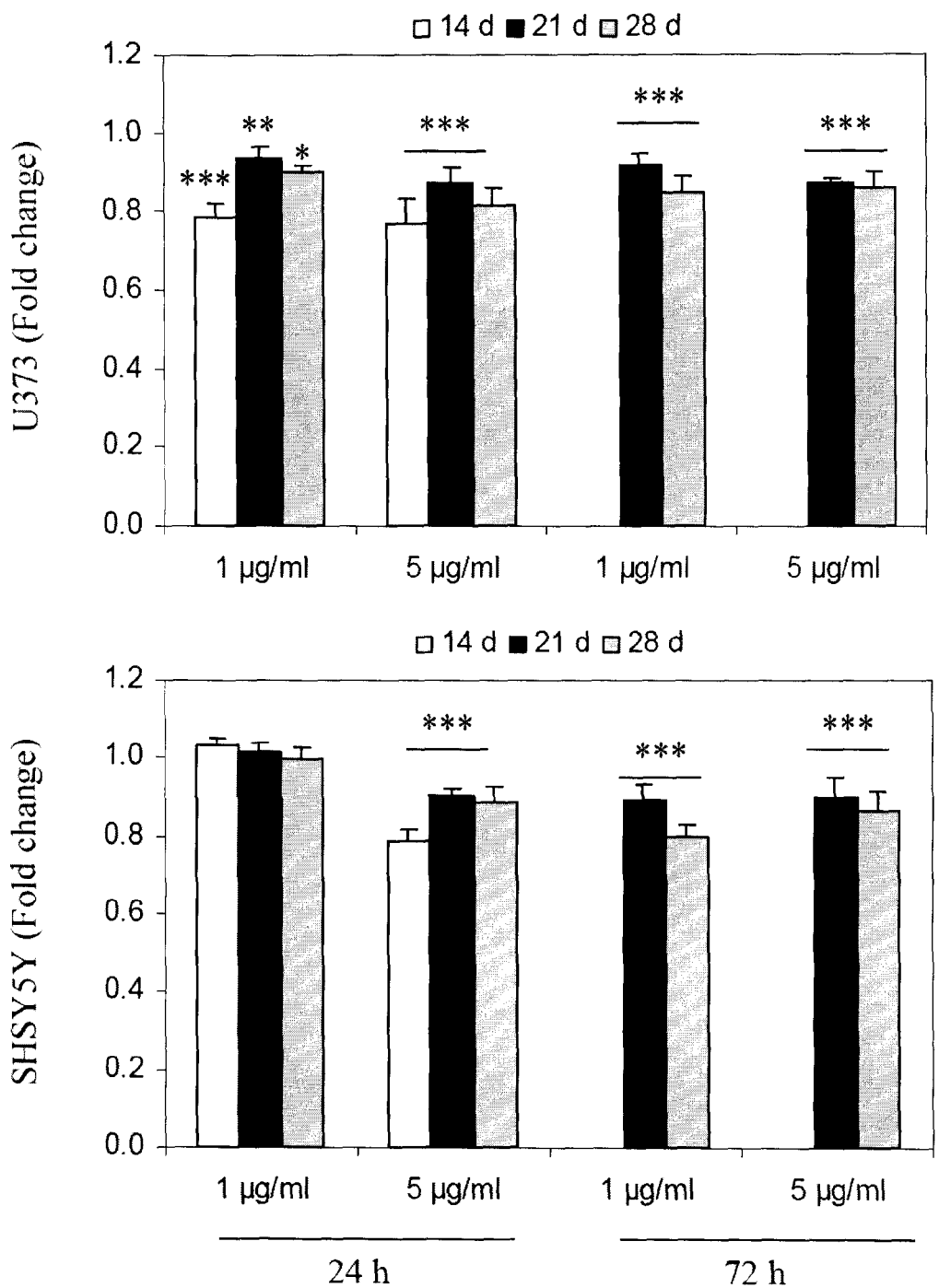

COMPOUNDS AND METHODS FOR TREATING CANCER AND VIRAL INFECTIONS

REFERENCE TO RELATED APPLICATIONS

This application is a national phase entry of co-pending PCT/CA2010/000281, filed Mar. 2, 2010, which claims priority from U.S. Provisional patent application Ser. No. 61/156,560 filed Mar. 2, 2009, each of these applications being incorporated herein by reference in their entirety.

FIELD OF THE APPLICATION

The present application relates to methods for treating cancer and viral infections.

BACKGROUND OF THE APPLICATION

Cancer is a class of diseases in which a group of cells display uncontrolled growth or division, invasion and sometimes metastasis. Most cancers form a tumour, but some, like leukemia, do not.

Treatments for viral infections have come to the forefront in view of the recent worldwide scare with H1N1 viral infections.

SUMMARY OF THE APPLICATION

Current chemotherapeutics affect only a small time zone during the cell division cycle. Typically, these drugs have cell kills of 2-5% in the active division cycle. The average cell division time in solid tumors is 90 to 120 days, in lymphomas, about 30 days, in leukemias, about 5 to 6 days. In solid tumors about 90% of the cells are in $G_o$. DNA synthesis is directly related to the speed of the cell cycle and correlates with the speed of ingestion of the amino acids into the DNA. By binding to amino acids, the compounds of the present application interfere with DNA synthesis and result in an effective treatment for cancer and viral infections.

Accordingly, the present application includes a method of treating cancer comprising administering to a subject in need thereof, an effective amount one or more compounds of Formula I, or pharmaceutically acceptable solvates or prodrugs thereof:

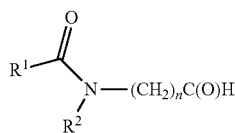
(I)

wherein
R$^1$ is selected from C$_{1-6}$alkyl, phenyl and naphthyl;
R$^2$ is selected from H and C(O)—R$^3$ and R$^3$ is selected from C$_{i-6}$alkyl, phenyl and naphthyl or R$^3$ and R$^1$ are linked to form, together with the atoms to which they are attached, a 5- or 6-membered ring that is optionally fused to a phenyl or naphthyl group;
n is 1, 2, 3 or 4; and
when R$^2$ is H, and n is 2, 3 or 4, the compound of Formula I optionally exists in cyclized form:

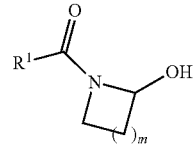

wherein m is 1, 2 or 3.

The present application also includes a use of one or more compounds Formula I, as defined above, or pharmaceutically acceptable solvates or prodrugs thereof, for treating cancer. Further, the present application includes a use of one or more compounds of Formula I, as defined above, or pharmaceutically acceptable solvates or prodrugs thereof, to prepare a medicament for treating cancer. Still further, the present application includes one or more compounds of formula I as defined above, or pharmaceutically acceptable solvates or prodrugs thereof, for use to treat cancer.

The present application includes a method of treating or preventing a viral infection comprising administering to a subject in need thereof, an effective amount of one or more compounds Formula I, or pharmaceutically acceptable solvates or prodrugs thereof:

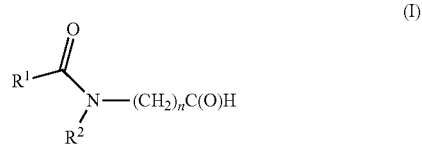
(I)

wherein
R$^1$ is selected from C$_{1-6}$alkyl, phenyl and naphthyl;
R$^2$ is selected from H and C(O)—R$^3$ and R$^3$ is selected from C$_{i-6}$alkyl, phenyl and naphthyl or R$^3$ and R$^1$ are linked to form, together with the atoms to which they are attached, a 5-or 6-membered ring that is optionally fused to a phenyl or naphthyl group;
n is 1, 2, 3 or 4; and
when R$^2$ is H, and n is 2, 3 or 4, the compound of Formula I optionally exists in cyclized form:

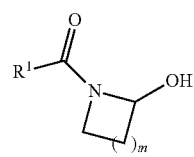

wherein m is 1, 2 or 3.

The present application also includes a use of one or more compounds of Formula I, as defined above, or pharmaceutically acceptable solvates or prodrugs thereof, for treating or preventing a viral infection. Further, the present application includes a use of one or more compounds of Formula I, as defined above, or pharmaceutically acceptable solvates or prodrugs thereof, to prepare a medicament for treating or preventing a viral infection. Still further, the present application includes one or more compounds of formula I as defined above, or pharmaceutically acceptable solvates or prodrugs thereof, for use to treat or prevent a viral infection.

In an embodiment of the application the compounds of the application are administered to the subject over an extended period of time (i.e. long term or chronic administration).

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

BRIEF DESCRIPTION OF THE DRAWINGS

The application will now be described in relation to the drawings in which:

FIG. 1 shows the results of the evaluation of human U373 and SHSY5Y cells following extended incubation with compound I(a) compared to a control. Cells were seeded in 96-well plates following incubation with the indicated concentration of compound I(a) for 14, 21 or 28 days. Cells incubated in the absence of compound for the same number of days served as controls. Mean absorbance values from eight wells are expressed as fold changes relative to control with the relative degree of variability between the samples indicated as error bars. *$p<0.05$, **$p<0.01$, #$p<0.001$, Students t-test.

DETAILED DESCRIPTION OF THE APPLICATION (I) Definitions

The term "alkyl" as used herein means straight and/or branched chain alkyl groups and includes methyl, ethyl, propyl, isopropyl, t-butyl, pentyl, hexyl and the like.

A phthalimido group is represented by the following formula:

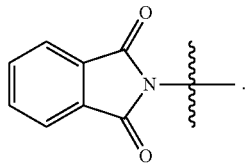 [SMILES: *N1C(=O)c2ccccc2C1=O]

In a naphthalimido group, an additional phenyl ring is fused to the phenyl ring of the phthalimido group.

The term "compounds of the application" as used herein refers to a compound of Formula I, or pharmaceutically acceptable solvates or prodrugs thereof. It is to be clear that the methods and uses of the present application includes pharmaceutically acceptable solvates or prodrugs of compounds of the application and mixtures comprising two or more of compounds of Formula I, pharmaceutically acceptable solvates of compounds of Formula I or pharmaceutically acceptable prodrugs of compounds of Formula I.

The term "pharmaceutically acceptable" means compatible with the treatment of animals, in particular, humans.

The term "solvate" as used herein means a compound of the Formula I, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions.

Compounds of the application include prodrugs. In general, such prodrugs will be functional derivatives of a compound of the application which are readily convertible in vivo into the compound from which it is notionally derived. In an embodiment of the application, prodrugs of the compounds of the application may be conventional esters formed with available hydroxy or amino groups. For example, an available OH or NH group in a compound of the invention may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In further embodiments, the prodrugs of the compounds of the invention are those in which one or more of the hydroxy groups in the compounds is masked as groups which can be converted to hydroxy groups in vivo. In a further embodiment, prodrugs of the compounds of the application are conventional imines, oximes, acetals, enol esters, oxazolidines or thiazolidines formed with the available aldehyde group. Conventional procedures for the selection and preparation of suitable prodrugs are described, for example, in "Design of Prodrugs" ed. H. Bundgaard, Elsevier, 1985 or are known to a person skilled in the art.

The term "subject" as used herein includes all members of the animal kingdom including human. The subject is suitably a human.

The term a "therapeutically effective amount", "effective amount" or a "sufficient amount" of a compound of the present application is a quantity sufficient to, when administered to the subject, including a mammal, for example a human, effect beneficial or desired results, including clinical results, and, as such, an "effective amount" or synonym thereto depends upon the context in which it is being applied. For example, in the context of disease, therapeutically effective amounts of the compounds of the present disclosure are used to treat, modulate, attenuate, reverse, or affect cancer or a viral infection in a mammal. An "effective amount" is intended to mean that amount of a compound that is sufficient to treat or inhibit the cancer or viral infection or a disease associated with the cancer or viral infection. The amount of a given compound of the present disclosure that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" of a compound of the present application is an amount which inhibits, suppresses or reduces a cancer or viral infection (e.g., as determined by clinical symptoms or the amount of cancer or virus) in a subject as compared to a control. As defined herein, a therapeutically effective amount of a compound of the present application may be readily determined by one of ordinary skill by routine methods known in the art.

As used herein, and as well understood in the art, "treating" or "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

Moreover, a "treatment" or "prevention" regime of a subject with a therapeutically effective amount of the compound of the present application may consist of a single administration, or alternatively comprise a series of applications. For example, the compound of the present application may be administered at least once a week. However, in another embodiment, the compound may be administered to the patient from about one time per week to one or more, for example one to four, times daily for a given treatment. The length of the treatment or prevention period depends on a variety of factors, such as the severity of the disease, the age of the patient, the concentration and the activity of the compounds of the present application, or a combination thereof. It will also be appreciated that the effective dosage of the compound used for the treatment or prevention may increase or decrease over the course of a particular treatment or prophylaxis regime. Changes in dosage may result and become apparent by standard diagnostic assays known in the art. In some instances, chronic administration may be required. The compounds of the present application may be administered before, during or after exposure to the virus or to detection or formation of the cancer.

"Palliating" a disease or disorder, means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a viral infection or manifesting a symptom associated with a viral infection.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(II) Therapeutic Methods and UsES

The present application includes a method of treating cancer comprising administering to a subject in need thereof, an effective amount of one or more compounds of Formula I, or pharmaceutically acceptable solvates or prodrugs thereof:

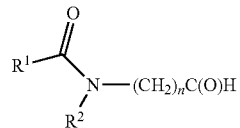

wherein
$R^1$ is selected from $C_{1-6}$alkyl, phenyl and naphthyl;
$R^2$ is selected from H and C(O)—$R^3$ and $R^3$ is selected from $C_{1-6}$alkyl, phenyl and naphthyl or $R^3$ and R' are linked to form, together with the atoms to which they are attached, a 5-or 6-membered ring that is optionally fused to a phenyl or naphthyl group;
n is 1, 2, 3 or 4; and
when $R^2$ is H, and n is 2, 3 or 4, the compound of Formula I optionally exists in cyclized form:

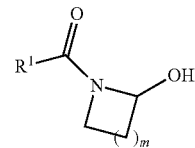

wherein m is 1, 2 or 3.

It is an embodiment of the application that $R^1$ is selected from phenyl, isobutyl, isopropyl and t-butyl. In a further embodiment $R^1$ is t-butyl.

It is another embodiment of the application that $R^1$ and $R^3$ are linked to form, together with the atoms to which they are attached, a 5-membered ring that is fused to a phenyl or naphthyl group to provide a phthalimido or a naphthalimido group. In further embodiment, $R^1$ and $R^3$ are linked to form, together with the atoms to which they are attached, a phthalimido group.

In another embodiment of the application, n is 2 or 3. In a further embodiment, n is 3.

In another embodiment, $R^2$ is H and the compound of Formula I exists in cyclized form:

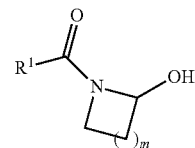

wherein m is 2 or 3. In a further embodiment m is 2.

In a further embodiment of the present application, the compound of Formula I is:
4-(1,3-dioxo-1,3-dihydro-2H-isoindol-2-yl)butanal (Ia); or
tent-butyl 2-hydroxypyrrolidine-1-carboxylate, I(b), or
a pharmaceutically acceptable solvate or prodrug thereof.

The present application also includes a use of one or more compounds of Formula I, as defined above, or pharmaceutically acceptable solvates or prodrugs thereof, for treating cancer. Further, the present application includes a use of one or more compounds of Formula I, as defined above, or pharmaceutically acceptable solvates or prodrugs thereof, to prepare a medicament for treating cancer. Still further, the present application includes one or more compounds of Formula I, as defined above, or pharmaceutically acceptable solvates or prodrugs thereof, for use to treat cancer.

In an embodiment of the application, the cancer is any form of neoplastic disease, including both tumour forming and non-tumour forming cancers. In a further embodiment, the cancer is a brain cancer. In a further embodiment the cancer is a neuroblastoma or an astrocytoma.

The present application includes a pharmaceutical composition for treating cancer comprising an effective amount of one or more of compounds of Formula I as defined above, or pharmaceutically acceptable solvates or prodrugs thereof, and a pharmaceutically acceptable carrier.

The present application also includes a method of treating or preventing a viral infection comprising administering to a subject in need thereof, an effective amount of one or more compounds of Formula I, or pharmaceutically acceptable solvates or prodrugs thereof:

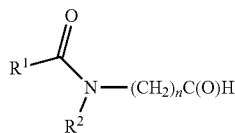

wherein $R^1$ is selected from $C_{1-6}$alkyl, phenyl and naphthyl;

$R^2$ is selected from H and C(O)—$R^3$ and $R^3$ is selected from $C_{1-6}$alkyl, phenyl and naphthyl or $R^3$ and $R^1$ are linked to form, together with the atoms to which they are attached, a 5-or 6-membered ring that is optionally fused to a phenyl or naphthyl group;

n is 1, 2, 3 or 4; and when $R^2$ is H, and n is 2, 3 or 4, the compound of Formula I optionally exists in cyclized form:

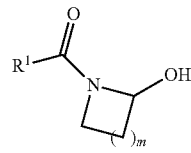

wherein m is 1, 2 or 3.

It is an embodiment of the application that $R^1$ is selected from phenyl, isobutyl, isopropyl and t-butyl. In a further embodiment $R^1$ is t-butyl.

It is another embodiment of the application that $R^1$ and $R^3$ are linked to form, together with the atoms to which they are attached, a 5-membered ring that is fused to a phenyl or naphthyl group to provide a phthalimido or a naphthalimido group. In further embodiment, $R^1$ and $R^3$ are linked to form, together with the atoms to which they are attached, a phthalimido group.

In another embodiment of the application, n is 2 or 3. In a further embodiment, n is 3.

In another embodiment, $R^2$ is H and the compound of Formula I exists in cyclized form:

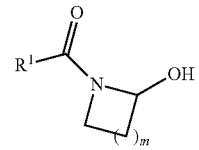

wherein m is 2 or 3. In a further embodiment m is 2.

In a further embodiment of the present application, the compound of Formula I is:

4-(1,3-dioxo-1,3-dihydro-2H-isoindol-2-yl)butanal (Ia); or tert-butyl 2-hydroxypyrrolidine-1-carboxylate, I(b), or a pharmaceutically acceptable solvate or prodrug thereof.

The present application also includes a use of one or more compounds of Formula I, as defined above, or pharmaceutically acceptable solvates or prodrugs thereof, for treating or preventing a viral infection. Further, the present application includes a use of one or more compounds of Formula I, as defined above, or pharmaceutically acceptable solvates or prodrugs thereof, to prepare a medicament for treating or preventing a viral infection. Still further, the present application includes one or more compounds of Formula I as defined above, or pharmaceutically acceptable solvates or prodrugs thereof, for use to treat or prevent a viral infection.

In an embodiment of the application, the viral infection is an influenza-type infection. In a further embodiment, the viral infection is an influenza A infection or an influenza B infection.

The present application includes a pharmaceutical composition for treating or preventing a viral infection comprising an effective amount of one or more of compounds of Formula I as defined above, or pharmaceutically acceptable solvates or prodrugs thereof, and a pharmaceutically acceptable carrier.

Some of the compounds of Formula I, as defined above, have at least one asymmetric centre. Where the compounds possess one asymmetric centre, they exist as enantiomers. Where the compounds possess more than one asymmetric centre, they exist as diastereomers. It is to be understood that all such isomers and mixtures thereof in any proportion are encompassed within the scope of the present application. It is to be understood that while the stereochemistry of the compounds may be as provided for in any given compound listed herein, such compounds may also contain certain amounts (e.g. less than 20%, preferably less than 10%, more preferably less than 5%) of compounds of the invention having alternate stereochemistry.

In an embodiment of the present application, the compounds of Formula I as defined above, or pharmaceutically acceptable solvates or prodrugs thereof, are prepared from known starting materials using procedures known in the art. For example, 4,4-diethooxybutan-1-amine, which is commercially available is readily mono or diacylated using standard procedures. Conversion of the diethoxy group to the corresponding aldehyde is performed by treatment with acid and if, $R^2$ is H, the resulting compound will typically cyclize in situ.

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 1991.

In accordance with the methods and uses of the application, the compounds of Formula I, as defined above, and/or pharmaceutically acceptable solvates and/or prodrugs thereof, are administered to a patient in a variety of forms depending on the selected route of administration, as will be understood by those skilled in the art. In an embodiment, compounds of Formula I, as defined above, and/or solvates and/or prodrugs thereof, are administered, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time. Conventional procedures and ingredients for the selection and preparation of suitable formulations are described, for example, in Remington's Pharmaceutical Sciences (2000-20th edition) and in The United States Pharmacopeia: The National Formulary (USP 24 NF19) published in 1999.

In an embodiment, compounds of Formula I, as defined above, and/or solvates and/or prodrugs thereof, are orally administered, for example, with an inert diluent or with an assimilable edible carrier, or are enclosed in hard or soft shell gelatin capsules, or are compressed into tablets, or are incorporated directly with the food of the diet. For oral therapeutic administration, the compound is incorporated, for example, with excipient and used in the form of ingestible tablets, buccal tablets, troches, capsules, elixirs, suspensions, syrups, wafers, and the like.

In another embodiment, compounds of Formula I, as defined above, and/or solvates and/or prodrugs thereof, are administered parenterally. For example, solutions of a compound of the application are prepared in water suitably mixed with a surfactant such as hydroxypropylcellulose. In an embodiment, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms.

The pharmaceutical forms suitable for injectable use include sterile aqueous solutions or dispersion and sterile powders for the extemporaneous preparation of sterile injectable solutions or dispersions. In all cases, the form must be sterile and must be fluid to the extent that easy syringability exists.

In a further embodiment, compositions for nasal administration are conveniently formulated as aerosols, drops, gels or powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

In a further embodiment, compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

In a further embodiment, compounds of Formula I, as defined above, and/or solvates and/or prodrugs thereof, are administered in the form of liposome delivery systems, such as small unilamellar vesicles, large unilamellar vesicles and multilamellar vesicles. Liposomes are, for example, formed from a variety of phospholipids, such as cholesterol, stearylamine or phosphatidylcholines.

In a further embodiment, compounds of Formula I, as defined above, and/or solvates and/or prodrugs thereof, are delivered by the use of monoclonal antibodies as individual carriers to which the compound molecules are coupled. In another embodiment, compounds of Formula I, as defined above, and/or solvates and/or prodrugs thereof, are coupled with soluble polymers as targetable drug carriers. Such polymers include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. In a further embodiment, compounds of Formula I, as defined above, and/or solvates and/or prodrugs thereof, are coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In an embodiment, compounds of Formula I, as defined above, and/or solvates and/or prodrugs thereof, are used alone or in combination with other known agents useful for treating cancer.

When used in combination with other agents useful in treating cancer, compounds of Formula I, as defined above, and/or solvates and/or prodrugs thereof, are suitably administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances.

The dosage of compounds of Formula I, as defined above, and/or solvates and/or prodrugs thereof, can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. In an embodiment, compounds of the application, and/or solvates and/or prodrugs thereof, are administered initially in a suitable dosage that is adjusted as required, depending on the clinical response. As a representative example, oral dosages of compounds of Formula I, as defined above, and/or solvates and/or prodrugs thereof, range between about 1 mg per day to about 400 mg per day for an adult, suitably about 1 mg per day to about 200 mg per day, more suitably about 1 mg per day to about 20 mg per day. When formulated for oral administration, the compounds are suitably in the form of tablets containing 0.25, 0.5, 0.75, 1.0, 5.0, 10.0, 20.0, 25.0, 30.0, 40.0, 50.0, 60.0, 70.0 75.0, 80.0, 90.0, 100.0 150, 200, 250, 300, 350 or 400 mg of active ingredient per tablet. Suitably, for oral administration, the compounds are suitably in the form of tablets containing 0.25, 0.5, 0.75, 1.0, 5.0 or 10.0, mg of active ingredient per tablet. In another embodiment, compounds of Formula I, as defined above, and/or solvates and/or prodrugs thereof, are administered in a single daily dose or the total daily dose is divided into two, three of four daily doses. If the compound of Formula I, as defined above, and/or solvates and/or prodrugs thereof, are to be administered transdermally, using, for example, those forms of transdermal skin patches that are well known to those skilled in the art, the dosage administration will be continuous rather than intermittent throughout the dosage range.

In an embodiment of the application, the compounds of Formula I, as defined above, and/or solvates and/or prodrugs thereof, are administered or used over an extended period of time, i.e. long term use or chronic use for both treating cancer or treating or preventing a viral infection. The term "long term" and "chronic" use or administration as used herein means that the compounds of Formula I, as defined above, and/or pharmaceutically acceptable solvates or prodrugs thereof, are administered to a subject on a continuous regular, long-term therapeutic basis. For example, the compounds of Formula I, as defined above, and/or pharmaceutically acceptable solvates or prodrugs thereof, are administered to a subject without substantial interruption, such as, for example, daily, weekly, alternate days, alternate weeks, for a time period of at least several weeks or months to several years, for the purpose of treating cancer in a subject needing treatment. In an embodiment of the application, the compounds of Formula I, as defined above, and/or pharmaceutically acceptable solvates or prodrugs thereof, are administered to a subject for at least about 2 months. In a further embodiment of the application, the compounds of Formula I, as defined above, and/or pharmaceutically acceptable solvates or prodrugs thereof, are administered to a subject on an indefinite basis, for example until such administration does not have a beneficial effect or treatment.

EXAMPLES

Example 1

Synthesis of 4-(1,3-dioxo-1,3-dihydro-2H-isoindol-2-yl)butanal (Ia)

Step 1 of 3: Preparation of 2-(4,4-diethoxybutylcarbamoyl)benzoic acid

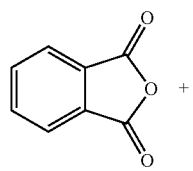

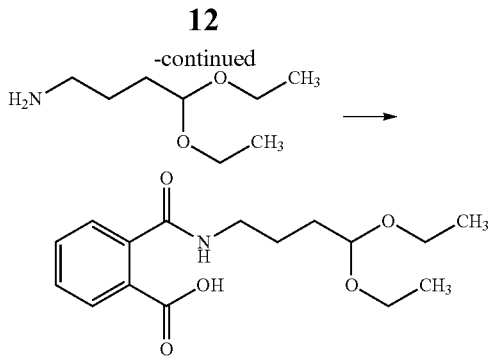

Materials:
(1) Phthalic Anhydride (Aldrich), 3.89 g (26.3 mmoles)
(2) 4,4-diethoxybutan-1-amine (Aldrich), 4.03 g (25.0 mmoles)
(3) N,N-dimethylaminopyridine (Aldrich), 30.5 mg (0.25 mmoles)
(4) Triethylamine (tech), 3.83 mL (27.3 mmoles)
(5) Tetrahyofuran (tech), 40.0 mL To a dry 100 mL round bottom flask was added tetrahydrofuran (40.0 mL), N,N-dimethylpyridin-4-amine (4.03 g), N,N-dimethylaminopyridine (30.5 mg) and triethylamine (3.83 mL). The solution was cooled to below 10° C. in an ice-water bath. Phthalic anhydride (3.89 g) was added portion-wise into the solution at below 10° C. A mild exotherm was observed. After addition, the solution was stirred at below 10° C. for half hour and them slowly warmed up to room temperature and stirring was continued for another hour. A small sample was taken and stripped to dryness under vacuum at room temperature. The residue was dissolved in CDCl₃ and a proton NMR spectrum was run. The result showed that complete conversion had been achieved. The remaining reaction mixture was stripped to dryness under vacuum at room temperature. The crude product was used directly for next step without further purification.

Step 2 of 3: Preparation of 2-(4,4-diethoxybutyl)-1H-isoindole-1,3(2H)-dione

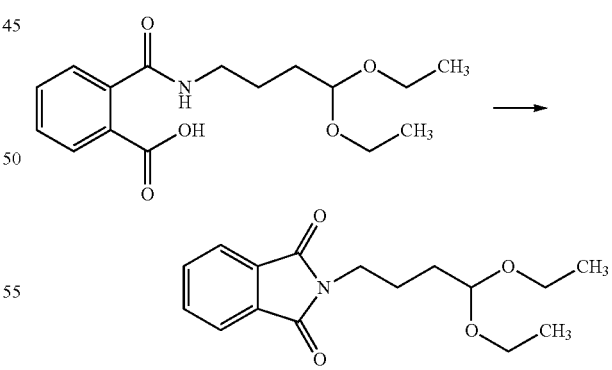

Materials:
(1) Step 1 product (crude), 25.0 mmoles
(2) Acetic anhydride (tech), 35.0 mL
(3) Sodium acetate (tech), 1.0 g
(4) Ethyl acetate (tech), 60 mL
(5) Saturated Sodium bicarbonate, 30.0 mL
(6) Sodium sulfate (tech), 5.0 g
(7) Ice, 200 g Acetic anhydride (35.0 mL) and sodium acetate (1.0 g) were added into the residue from step. The slurry was heated to 110° C. and stirred at this temperature for three hours. A small sample was quenched into a mixture of ethyl acetate and saturated sodium bicarbonate. The organic phase was separated and stripped to dryness. The residue was dissolved in CDCl₃ and a proton NMR was run. The result showed that complete conversion had been achieved.

The remaining reaction solution was cooled to room temperature and poured into an ice-water mixture (200 g). After stirring for about 2 hours, the solution was extracted with ethyl acetate (3×20 mL). The combined organic phase was washed with saturated sodium bicarbonate (2×15 mL) and dried with sodium sulfate (5.0 g). The filtrate was stripped to dryness to give the crude product 2 in overall 90% yields for step 1 and 2.

$^1$H-NMR (CDCl$_3$): 7.85 (m, 2H), 7.71 (m, 2H), 4.52 (t, 5.7 Hz, 1H), 3.72 (t, 7.2Hz, 2H), 3.62 (m, 2H), 3.50 (m, 2H), 1.76 (m, 2H), 1.66 (m, 2H) and 1.19 (t, 7.2 Hz, 6H).

Step 3 of 3: Preparation of 4-(1,3-dioxo-1,3-dihydro-2H-isoindol-2-yl)butanal, I(a)

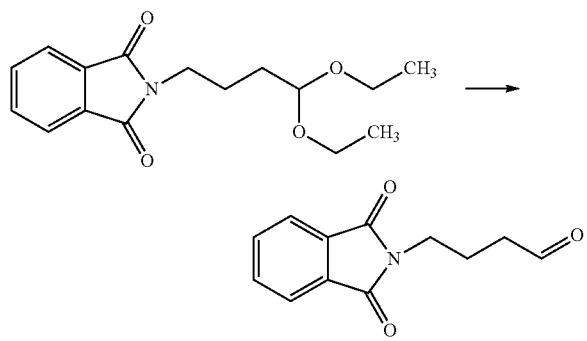

Materials:

(1) Step 2 product (crude), 4.55 g (15.6 mmoles)

(2) Tetrahyofuran (tech), 35.0 mL (3) Toluenesulfonic acid mono hydrate (Aldrich), 150 mg (4) Ethyl acetate (tech), 50 mL (5) Saturated Sodium bicarbonate, 20.0 mL;

(6) Sodium sulfate (tech), 5.0 g (7) Water, 3.5 mL (8) Brine, 20 mL

To a 100 mL round bottom flask was added step 2 product (4.55 g) followed by adding tetrahydrofuran (35.0 mL), water (3.5 mL) and toluenesulfonic acid (150 mg). The solution was stirred at room temperature under nitrogen. The reaction progress was monitored by NMR. After three days a completed conversion had been achieved. The solution was diluted with ethyl acetate (50.0 mL) and washed with saturate sodium bicarbonate (20 mL), brine (20 mL) and dried with sodium sulfate (5.0 g). The filtrate was stripped to dryness and gave the product I(a) in 86% yield in over 90% purity based on NMR.

$^1$H-NMR (CDCl$_3$): 9.78 (t, 1.2 Hz, 1H), 7.85 (m, 2H), 7.73 (m, 2H), 3.75 (t, 6.9 Hz, 2H), 2.55 (td, 6.9 Hz, 1.2 Hz, 2H) and 2.03 (m, 2H).

Example 2

Synthesis of tert-butyl 2-hydroxypyrrolidine-1-carboxylate I(b)

Step 1 of 2: Preparation of tert-butyl (4,4-diethoxybutyl)carbamate

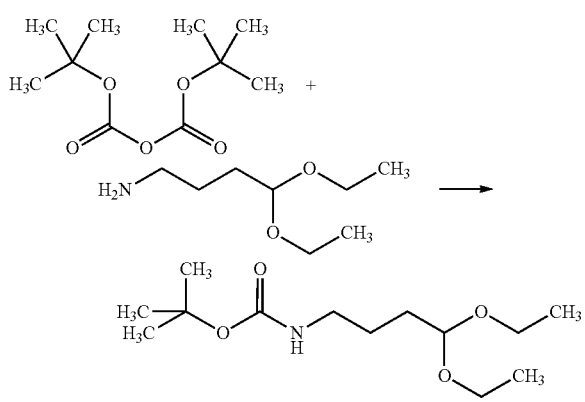

Materials:

(1) 4,4-diethoxybutan-1-amine (Aldrich), 16.125 g (0.100 moles)

(2) di-tert-butyl dicarbonate (Aldrich), 21.825 g (0.100 moles)

(3) Triethylamine (tech), 1.0 mL (7.2 mmoles)

(4) Tetrahyofuran (tech), 30.0 mL

To a dry 100 mL round bottom flask was added tetrahydrofuran (30.0 mL), di-tert-butyl dicarbonate (21.825 g) and triethylamine (1.0 mL). The solution was cooled to below 10° C. in an ice-water batch. 4-Diethoxybutan-1-amine (16.125 g) was added slowly into the solution at below 10° C. A mild exotherm was observed. After addition the solution was stirred at below 10° C. for a half hour and them slowly warmed up to room temperature and stirring continued for 1.5 hours. An in-process QC (TLC, heptane: ethyl acetate, 7:3) showed a completed conversion had been achieved. The reaction was stripped to dryness under vacuum at room temperature. The crude product was used directly for next step without further purification. The yield was quantitative. The crude product was identified based on NMR data.

$^1$H-NMR (CDCl$_3$, ppm): 4.49 (t, 5.1Hz, 1H), 3.64 (m, 2H), 3.49 (m, 2H), 3.14 (m, 2H), 1.66~1.52 (m, 2H), 1.44 (s, 9H) and 1.21 (t, 7.2Hz, 6H).

Step 2 of 2: Preparation of tert-butyl 2-hydroxypyrrolidine-1-carboxylate, I(b)

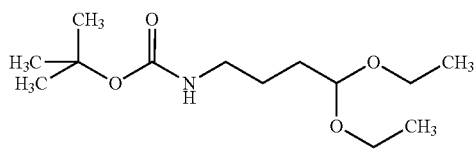

-continued

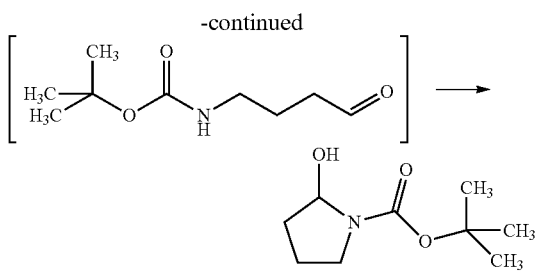

Materials:
(1) Step 1 product (crude), 5.0 g (0.019 moles)
(2) Toluenesulfonic acid monohydrate (Aldrich), 0.150 g (0.79 mmoles)
(3) Tetrahyofuran (tech), 35.0 mL
(4) DI-water, 5.0 mL
(5) Saturated Sodium bicarbonate, 2.0 mL
(6) Sodium sulfate (tech), 2.0 g
(7) Ethyl acetate (tech), 20 mL To a 50 mL round flask, was added the step 1 product (5.0 g), tetrahydrofuran (35.0 mL) and DI-water (5.0 mL). Toluenesulfonic acid monohydrate (0.150 g) was added and the solution was stirred at room temperature over three hours. A small sample was taken and stripped to dryness. The residue was dissolved in $CDCl_3$ and proton NMR was run. The result showed a completed conversion had been achieved.

Saturated sodium bicarbonate (2.0 mL) was added to the reaction and tetrahydrofuran was stripped off under vacuum at room temperature. Ethyl acetate (20.0 mL) was added to dissolve the residue. After removing the water phase, the organic phase was dried over sodium sulfate (2.0 g). The solids were filtered off and the filtrate was concentrated to dryness under vacuum at below 40° C. to give the crude product in about 87% yield. The major compound from the crude product was identified purely based on NMR data.

$^1$H-NMR ($CDCl_3$, ppm): 5.48 (m, 1H), 3.49 (m, 2H), 3.28 (m, 2H), 1.90 (m, 2H), 1.48 (s, 9H).

Example 3

Evaluation of the Activity of Compounds in Indicator Human Neuroglioma and Neuroblastoma Cell Lines Compound preparation: Stock solutions of test compounds were prepared in dimethylsulfoxide (DMSO) at 250 mg/ml. Working concentrations of 10 mg/ml were subsequently prepared from the stock solution and stored in 50 µl aliquots at −20° C. until used.

Cells and cell culture: Proof-of-principle studies in this example focused on two human brain cancer cell lines, namely SH-SY5Y neuroblastoma cells and U373 astroglioma cells. SH-SY5Y cells were derived from a metastatic bone tumour from a four year old female patient, while U373 glioblastoma-astrocytoma cells are a recognized in vitro model of human malignant glioma. Both cells were maintained in (50:50) F12:DMEM medium supplemented with 10% fetal calf serum (FCS) and antibiotics in a humidified, 5% $CO_2$ environment. Cells were passaged as required by trypsinization.

Assays conditions: The effects of the test compounds were assessed following acute and chronic exposure conditions. For acute studies, cells were seeded in 96-well plates in quadruplicate at a comparatively higher density (1×104 cells/well) and incubated with serial dilutions of the test compounds for 24 h prior to analysis of cell proliferation and/or viability. For chronic studies, cells were seeded at a comparatively lower density (2×10³ cells/well) and incubated with the test compounds for 72 h. The test compounds were evaluated over a broad range of concentrations (0, 0.5, 1, 5, 10, 50, 100 and 250 µg/ml) with cells treated with equivalent concentrations of vehicle (DMSO) serving as controls.

Cell proliferation assay: Cell proliferation was assessed using a standard colorimetric indicator of metabolic activity (CIMA) assay. In this assay, the reduction of yellow tetrazolium salt (MTT) to purple formazan by mitochondrial reductase enzymes in viable cells was evaluated as a measure of metabolic activity to determine the extent of cell proliferation within a culture. The resulting colour change that conferred a change in absorbance was quantified using a spectrophotometer ($\lambda$=500-600). Samples were diluted as required to ensure that values obtained with the MTT assay fell within the linear range of the protocol. Qualitative microscopic evaluation of treated cultures was used to determine if overt cytotoxicity was present and to supplement the quantitative CIMA data.

Results:

U373 astrocytoma cells: Neither overt cell death nor significant reductions in MTT activity were observed with compound I(a) or I(b) under acute and chronic treatment conditions.

SH-5YSY neuroblastoma cells: Both compound I(a) and I(b) produced an approximately 30% decrease in MTT activity under acute treatment conditions at a dose of 0.25 mg/ml. No significant change in MTT activity was observed at the other concentrations evaluated.

Under chronic treatment conditions, significantly decreased MTT activity was observed at 50, 100 and 250 µg/ml doses. For compound I(a), this decrease averaged 25% at each of the three concentrations. For compound I(b), maximal decreases of 47% were observed at the 250 µg/ml dose compared to 25% at 50 and 100 µg/ml concentrations.

Analysis: Proof-of-principle studies indicate that neither compound I(a) nor compound I(b) exhibited profound cytostatic/cytotoxic activity in either of the test cell lines, although cell-specific differences in efficacy were observed. The activity detected was insufficient to estimate true $LD_{50}$ concentrations for either compound. It may be concluded for the cell lines evaluated that the $LD_{50}$ of compound I(a) exceeds 0.25 mg/ml in both acute and chronic regimens, while the $LD_{50}$ of compound I(b) may approach 0.25 mg/ml in select cell types under chronic conditions.

Example 4

Evaluation of the Cytostatic and Cytotoxic Activity of Test Compounds in a Diverse Array of Human Neuroglioma and Neuroblastoma Cell Lines Compound preparation: Stock solutions of test compounds were prepared in dimethylsulfoxide (DMSO) at 250 mg/ml. Working concentrations of 10 mg/ml were subsequently prepared from the stock solution and stored in 50 µl aliquots at −20° C. until used.

Cells and cell culture: Three classes of cells were evaluated: 1) neuroblastoma cells, 2) neuroglioma cells, and 3) non-transformed human neurons (see below). All cells were maintained in appropriate culture medium supplemented with 10% fetal calf serum (FCS) and antibiotics in a humidified, 5% $CO_2$ environment. Cells were passaged as required by trypsinization.

| Neuroglioma and Neuroblastoma cell lines: | | |
|---|---|---|
| Type: | Designation | Origin/Properties |
| Neuroblastoma | IMR32 | neuroblast from abdominal mass, male |
|  | NG108 | neuroblastoma-neuroglioma fusion |
|  | NSC34 | motor neuron, male |
| Neuroglioma | U251 | malignant glioma |
|  | U118 | Grade III malignant astrocytoma, male |
|  | U138 | Grade III malignant astrocytoma, male |
|  | D32 | benign glioma |
|  | D37 | benign glioma |
|  | TP483 | malignant glioma |
|  | SW1088 | astrocytoma, male |
|  | U87 | Grade III malignant astrocytoma, female |
| Non-tumour | HCN-1 | cortical neuron (megalencephalic), male |
|  | HCN-2 | cortical neuron (megalencephalic), male |

Assay conditions: The effects of the test compounds were assessed following acute and chronic exposure conditions. For acute studies, cells were seeded in 96-well plates in quadruplicate at a comparatively higher density ($1\times10^4$ cells/well) and incubated with serial dilutions of the test compounds for 24 h prior to analysis of cell proliferation and/or viability. For chronic studies, cells were seeded at a comparatively lower density ($2\times10^3$ cells/well) and incubated with test compounds for 72 h. Each compound was evaluated over a broad range of concentrations (0, 0.5, 1, 5, 10, 50, 100 and 250 μg/ml) with cells treated with equivalent concentrations of vehicle (DMSO) serving as controls.

Cell proliferation assay: Cell proliferation was assessed using a standard colorimetric indicator of metabolic activity (CIMA) assay. In this assay, the reduction of yellow tetrazolium salt (MTT) to purple formazan by mitochondrial reductase enzymes in viable cells was evaluated as a measure of metabolic activity to determine the extent of cell proliferation within a culture. The resulting colour change that conferred a change in absorbance was quantified using a spectrophotometer ($\lambda=500$-$600$). Samples were diluted as required to ensure that values obtained with the MTT assay fell within the linear range of the protocol. Qualitative microscopic evaluation of treated cultures was used to determine if overt cytotoxicity was present and to supplement the quantitative CIMA data.

Results:
Neurons:

In general, when effects were observed there were more pronounced following treatment with compound I(a) than compound I(b). Cytostatic/cytotoxic effects were most commonly observed at the highest test concentration of 250 μg/ml at both 24 and 72 h post-treatment. Cytostatic/cytotoxic effects were only observed at 24 h post-treatment with this concentration. These observations applied to both transformed and non-transformed cells, suggesting that the effect was due to general toxicity rather than a tumour-specific process. Both compound I(a) and I(b) induced dose-dependent decreases in viability/proliferation for all three transformed neuronal cell lines at 72 h post-treatment. These decreases were statistically significant but associated with an $LD_{50}<0.25$ mg/ml only in the case of NSC34 motor neurons treated with compound I(a).

Astrocytes:

As with neurons, when effects were observed they were generally more pronounced following treatment with compound I(a) than compound I(b). Cytostatic/cytotoxic effects were most commonly observed at the highest test concentration of 250 μg/ml. Decreases in viability/proliferation were statistically significant and associated with an $LD_{50}<0.25$ mg/ml only in the case of U87 and U138 cells. For both compounds, an $LD_{50}<0.1$ mg/ml was not detected in any of the cell lines evaluated nor was an $LD_{50}<0.25$ mg/ml detected in the acute treatment regimen with any cell line.

Example 5

Evaluation of the Cytostatic and Cytotoxic Activity of Test Compounds in a Broader Spectrum of Cancer Cell Types Compound preparation: Stock solutions of the test compounds were prepared in dimethylsulfoxide (DMSO) at 250 mg/ml. Working concentrations of 10 mg/ml were subsequently prepared from the stock solution and stored in 50 μl aliquots at −20° C. until used.

Cells and cell culture: Seven classes of tumours represented by a minimum of two different cell lines were evaluated: 1) breast, 2) lung, 3) colon, 4) prostate, 5) renal/hepatic, 6) ovarian/uterine, and 7) lymphoma cells (see below). Primary human dermal fibroblasts served as a representative non-transformed, non-cancerous cell type. All cells were maintained in appropriate culture medium supplemented with 10% fetal calf serum (FCS) and antibiotics in a humidified, 5% $CO_2$ environment. Cells were passaged as required by trypsinization.

| Tumour classes assayed: | | |
|---|---|---|
| Tumour Type | Designation | Origin/Properties |
| Breast | BT-20 | mammary gland carcinoma, female |
|  | BT-474 | invasive ductal carcinoma, female |
|  | MCF-7 | mammary gland adenocarcinoma |
| Lung | H1299 | metastatic non-small cell lung carcinoma, male |
|  | A549 | lung carcinoma, male |
| Colon | HT29 | primary colorectal adenocarcinoma, female |
|  | HCT116 | colorectal carcinoma, male |
| Prostate | DU145 | metastatic carcinoma, male |
|  | PC3 | adenocarcinoma, male |
| Renal/Hepatic | HepG2 | hepatocellular carcinoma, male |
|  | 786-0 | renal cell adenocarcinoma, male |
| Ovarian/Uterine | SK-O-V3 | ovarian adenocarcinoma, female |
|  | OVCAR5 | ovarian adenocarcinoma, female |
| Lymphoma | THP-1 | acute monocytic leukemia, male |
|  | U937 | histiocytic lymphoma, male |
|  | SupT1 | T lymphoblastic leukemia |
| Non-tumour | CCD1079SK | normal dermal fibroblast |

Assay conditions: The effects of the test compounds were assessed following acute and chronic exposure conditions. For acute studies, cells were seeded in 96-well plates in quadruplicate at a comparatively higher density ($1\times10^3$ cells/well) and incubated with serial dilutions of the compound for 24 h prior to analysis of cell proliferation and/or viability. For chronic studies, cells were seeded at a comparatively lower density ($2\times10^3$ cells/well) and incubated with the compound for 72 h. Each compound was evaluated over a broad range of concentrations (0, 0.5, 1, 5, 10, 50, 100 and 250 μg/ml) with cells treated with equivalent concentrations of vehicle (DMSO) serving as controls.

Cell proliferation assay: Cell proliferation was assessed using a standard colorimetric indicator of metabolic activity (CIMA) assay. In this assay, the reduction of yellow tetrazolium salt (MTT) to purple formazan by mitochondrial reductase enzymes in viable cells was evaluated as a measure of metabolic activity to determine the extent of cell proliferation within a culture. The resulting colour change that conferred a change in absorbance was quantified using a spectrophotometer (λ=500-600). Samples were diluted as required to ensure that values obtained with the MTT assay fell within the linear range of the protocol. Qualitative microscopic evaluation of treated cultures was used to determine if overt cytotoxicity was present and to supplement the quantitative CIMA data.

Results: Both compound I(a) and I(b) exhibited their most pronounced effects in lymphoma-derived cells, meeting the criteria of a change in MTT activity of 20-30% over a range of concentrations. Several other cell lines were similarly affected at the highest concentration of compound, but no specific pattern or preferential inhibition of a specific tumour cell type other than lymphomas was observed.

Example 6

Long Term Anti-cancer Properties of Compound I(a)

Compound preparation: Stock solutions of the test compound were prepared in dimethylsulfoxide (DMSO) at 250 mg/ml. Working concentrations of 10 mg/ml were subsequently prepared from the stock solution and stored in 50 µl aliquots at −20° C. until used. Compound I(a) was termed CMPD A (LI568-026-02).

Cells and cell culture: Two human brain cancer cell lines were used in the study: SH-SY5Y neuroblastoma cells and U373 astroglioma cells. Both cell lines were maintained in appropriate culture medium supplemented with 10% fetal calf serum (FCS) and antibiotics in a humidified, 5% $CO_2$ environment. Cells were passaged as required by trypsinization.

Assay conditions: The effects of the test compound were assessed under long term exposure conditions. Cells were propagated as normal in $T_{25}$ flasks in complete culture media supplemented with comparatively low concentrations of the compound (0, 1 and 5 µg/ml) for 28 days. At various times post-exposure, changes in proliferation rates were assessed using a standard CIMA assay.

Cell proliferation assay: Cell proliferation/viability was assessed by standard tetrazole reduction assay, a measure of metabolic function that evaluates mitochondrial activity to determine the extent of cell proliferation or viability within a culture. The resulting colour change that conferred a change in absorbance was quantified using a spectrophotometer (λ=500-600). Samples were diluted as required to ensure that values obtained with the MTT assay fell within the linear range of the protocol. Qualitative microscopic evaluation of treated cultures was used to determine if overt cytotoxicity was present and to supplement the quantitative CIMA data. For the current study, cells that have been exposed to the compound were seeded in 96-well plates and proliferation rates measured over 24 and 72 h periods for comparison to that of similarly aged untreated cells.

Results: Data for the two cell lines is represented graphically in FIG. 1 with additional data in Table 1. As with the shorter term trials (Examples 2-4), neither of the test concentrations proved to be a 50% lethal dose ($LD_{50}$). Both cell lines, however, did respond to compound I(a) in a similar manner and exhibited an average decrease in activity of approximately 20%. Although relatively limited, this decrease was statistically significant. Of note, differences between the two concentrations, or between incubation periods, were minimal. The cells disintegrated after several days and the cell kill was throughout the cell cycle, including $G_o$.

Example 7

Evaluation of the Anti-Influenza Activity of Test Compounds

Compound preparation: Stock solutions of the test compounds were prepared in dimethylsulfoxide (DMSO) at 250 mg/ml. Working concentrations of 10 mg/ml were subsequently prepared from the stock solution and stored in 50 µl aliquots at −20° C. until used. The test compounds were compound I(a) and I(b) and had molecular structures as identified below.

Cells and viruses: Both primary chicken embryonic fibroblasts (CEF) and Madin-Darby canine kidney (MDCK) cells were evaluated in this study. Both cell lines produced similar results in preliminary trials; therefore, MDCK cells were selected for subsequent experiments. Both cells were maintained in the appropriate culture medium supplemented with 10% fetal calf serum (FCS) and antibiotics in a humidified, 5% $CO_2$ environment. Cells were passaged as required by trypsinization. For infection, cells were cultured in serum-free, minimum essential medium (MEM) supplemented with BSA and trypsin. Two strains of influenza were evaluated: 1) Influenza A (strain A/PR/8/34), a tissue culture adapted H1N1 serotype; and 2) Influenza B (strain B/Lee/40). Both viruses are tissue-cultured adapted to support an in vitro assay format.

Assay conditions: The effects of both compounds were assessed in a prophylactic regimen in which cells were pre-treated with a serial dilution of the test compound (0, 0.5, 1, 5, 10, 25, 50 and 100 µg/ml) for 24 h prior to infection. For assay, MDCK cells ($3 \times 10^4$ cells/well) were seeded in triplicate wells of 24-well culture plates and grown to 80% confluence, Cells were pre-treated with the test compound for 24 hr prior to infection, washed and then incubated with 500 µl of infection medium (MOI=0.1) for 4 h at 37° C. Cells were again washed and then overlaid with 1% agar containing the test compound. Cytopathic effects (CPE) indicative of virus replication were visually evaluated over a one week time-course. Consistent with literature reports, CPE were easily detected with 48 hpi; thus, time-frames for replicate experiments were shortened to 48 h. CPE were evaluated by microscopy and the extent of damage to the monolayer scored according to a graduated scale where 1 indicated little or no damage and 6 indicated complete loss of monolayer integrity (Table 2). Individual infections were repeated in four independent trials.

Cytotoxicity assay: Cells were incubated with test compound for 24 or 72 h prior to evaluation of cell viability. Cytotoxicity was assessed using a standard colorimetric indicator of metabolic activity (CIMA) assay. In this assay, the reduction of yellow tetrazolium salt (MTT) to purple formazan by mitochondrial reductase enzymes in viable cells was evaluated as a measure of metabolic activity to determine the extent of cell proliferation within a culture. The resulting colour change that conferred a change in absorbance was quantified using a spectrophotometer (λ=500-600). Samples were diluted as required to ensure that values obtained with the MTT assay fell within the linear range of the protocol. Qualitative microscopic evaluation of treated cultures was used to determine if overt cytotoxicity was present and to supplement the quantitative CIMA data.

Results: The results of the study are summarized in Table 3. In general, treatment with comparatively lower concentrations of I(a) resulted in a mild to moderate reduction in CPE following infection with either Influenza A or B strains. This effect was more prominent with the Influenza A strain than with Influenza B, and most evident earlier in the infection time-course. At least part of the increased CPE observed with concentrations of Compound A≥25 µg/ml may be attributed to toxicity associated with the compound itself at these higher concentrations (Table 4).

The results obtained with I(b) mirrored that of I(a) in that lower concentrations more greatly reduced CPE following Influenza A infection, and in that this reduction was greater at 24 hpi than at 48 hpi. However, I(b) treatment had little impact on CPE following Influenza B infection and did not evidence cytotoxicity at higher concentrations.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

|  | 24 h | | | 72 h | | |
|---|---|---|---|---|---|---|
|  | 0 µg/ml | 1 µg/ml | 5 µg/ml | 0 µg/ml | 1 µg/ml | 5 µg/ml |
|  | AVERAGE | | | | | |
| U373 | | | | | | |
| 14 d | 0.569 | 0.446 | 0.437 | — | — | — |
| 21 d | 0.617 | 0.575 | 0.539 | 0.547 | 0.502 | 0.478 |
| 28 d | 0.567 | 0.510 | 0.461 | 0.598 | 0.507 | 0.514 |
|  | SD | | | | | |
| 14 d | 0.013 | 0.020 | 0.036 | — | — | — |
| 21 d | 0.025 | 0.020 | 0.022 | 0.020 | 0.015 | 0.005 |
| 28 d | 0.050 | 0.011 | 0.027 | 0.023 | 0.025 | 0.025 |
|  | AVERAGE | | | | | |
| SHSY5Y | | | | | | |
| 14 d | 0.492 | 0.508 | 0.388 | — | — | — |
| 21 d | 0.307 | 0.311 | 0.277 | 0.300 | 0.268 | 0.269 |
| 28 d | 0.601 | 0.597 | 0.531 | 0.489 | 0.389 | 0.423 |
|  | SD | | | | | |
| 14 d | 0.023 | 0.009 | 0.012 | — | — | — |
| 21 d | 0.011 | 0.008 | 0.006 | 0.008 | 0.011 | 0.015 |
| 28 d | 0.016 | 0.018 | 0.025 | 0.015 | 0.016 | 0.024 |

TABLE 2

| Score | CPE |
|---|---|
| 1 | Complete monolayer with few gaps or dead cells |
| 2 | Some gaps in the monolayer; dead cells more evident |
| 3 | Increasing number of gaps in the monolayer concurrent with dead cells |
| 4 | Gaps widely distributed throughout the monolayer and of increasing size |
| 5 | Large holes forming as smaller gaps merge; copious dead cells evident |
| 6 | Monolayer integrity lost. Small islands of attached cells amid predominantly dead cells. |

TABLE 3

|  | 24 hpi | | | | 48 hpi | | | |
|---|---|---|---|---|---|---|---|---|
|  | Influenza A | | Influenza B | | Influenza A | | Influenza B | |
| Conc. (µg/ml) | Compd 1(a) | Compd 1(b) | Compd 1(a) | Compd 1(b) | Compd 1(a) | Compd 1(b) | Compd 1(a) | Compd 1(b) |
| Mock [1] | 1 | 1 | 1 | 1 | 2 | 2 | 1 | 1 |
| DMSO [2] | 1 | 1 | 1 | 1 | 2 | 2 | 1 | 1 |
| virus alone [3] | 3 | 3 | 4 | 4 | 4 | 4 | 5 | 5 |
| Virus + DMSO [4] | 3 | 3 | 4 | 4 | 4 | 4 | 4 | 4 |
| 0.5 | 1 [5] | 1 | 3 | 3 | 4 | 2 | 3 | 3 |
| 1.0 | 1 | 1 | 3 | 4 | 3 | 2 | 3 | 4 |
| 5.0 | 1 | 1 | 2 | 4 | 3 | 3 | 3 | 4 |
| 10 | 1 | 3 | 2 | 3 | 3 | 4 | 3 | 4 |
| 25 | 1 | 3 | 4 | 4 | 3 | 4 | 4 | 4 |
| 50 | 3 | 3 | 4 | 3 | 5 | 4 | 5 | 3 |
| 100 | 4 | 3 | 5 | 4 | 5 | 4 | 6 | 3 |

[1] mock: untreated and uninfected cells

[2] DMSO: uninfected cells pre-treated with vehicle alone (1%)

[3] virus alone: untreated, influenza-infected cells

[4] virus + DMSO: cells pre-treated with vehicle (1%) then infected with influenza

[5] bold: CPE in wells pre-treated with Compound 1(a) or 1(b) was less then that observed in controls

TABLE 4

| Conc. (μg/ml) | Compound 1(a) 24 h[1] | 72 h | Compound 1(b) 24 h | 72 h |
|---|---|---|---|---|
| 0 | 1.11[2] | 1.11 | 1.01 | 1.00 |
| 0.5 | 1.09 | 1.05 | 1.02 | 0.99 |
| 1.0 | 1.24 | 0.99 | 1.07 | 1.00 |
| 5.0 | 1.18 | 1.15 | 1.09 | 0.94 |
| 10 | 1.15 | 1.01 | 1.00 | 0.97 |
| 25 | 1.06 | 0.96 | 1.08 | 1.04 |
| 50 | 1.08 | 0.71[3] | 1.13 | 0.99 |
| 100 | 0.98 | 0.56 | 1.09 | 0.89 |

[1]Toxicity was evaluated after 24 or 72 h of exposure to the test compound to MDCK cells
[2]Values are expressed as fold changes relative to vehicle controls
[3]Bold: decreases exceeding 25% of control values are considered to be a toxic response

What is claimed is:

1. A method of treating cancer comprising administering to a subject in need thereof, an effective amount of a compound of Formula I, or pharmaceutically acceptable solvates or prodrugs thereof:

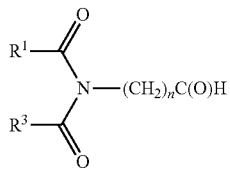

(I)

wherein
$R^3$ and $R^1$ are linked to form, together with the atoms to which they are attached, a 5- or 6-membered ring that is optionally fused to a phenyl or naphthyl group; and
n is 1, 2, 3 or 4;
wherein the cancer is selected from brain cancer, lung cancer, breast cancer, colon cancer prostate cancer, renal cancer, hepatic cancer, uterine cancer, ovarian cancer, lymphoma and cancer derived from lymphoma cells.

2. The method of claim 1, wherein $R^1$ and $R^3$ are linked to form, together with the atoms to which they are attached, a 5-membered ring that is fused to a phenyl or naphthyl group, to provide a phthalimido or a naphthalimido group.

3. The method of claim 1, wherein n is 2 or 3.

4. The method of claim 1, wherein the compound of Formula I is:

4-(1,3-dioxo-1,3-dihydro-2H-isoindol-2-yl) butanal (Ia); or a pharmaceutically acceptable solvate or prodrug thereof.

5. The method according to claim 1, wherein the cancer is a brain cancer.

6. The method according to claim 1, wherein the one or more compounds of Formula I, or pharmaceutically acceptable solvates or prodrugs thereof, are administered to the subject long term.

7. The method of claim 1, wherein the cancer is lymphoma or from lymphoma-derived cells.

* * * * *